United States Patent
Roop

(10) Patent No.: US 10,925,721 B2
(45) Date of Patent: Feb. 23, 2021

(54) OPTICAL IMPLANTABLE MEMBER

(71) Applicant: Prakhyat Roop, Meerut (IN)

(72) Inventor: Prakhyat Roop, Meerut (IN)

( * ) Notice: Subject to any disclaimer, the term of this patent is extended or adjusted under 35 U.S.C. 154(b) by 160 days.

(21) Appl. No.: 15/535,064

(22) PCT Filed: Aug. 13, 2015

(86) PCT No.: PCT/IB2015/056159
§ 371 (c)(1),
(2) Date: Jun. 12, 2017

(87) PCT Pub. No.: WO2016/132185
PCT Pub. Date: Aug. 25, 2016

(65) Prior Publication Data
US 2017/0348092 A1 Dec. 7, 2017

(30) Foreign Application Priority Data
Feb. 16, 2015 (IN) .............................. 433/DEL/2015

(51) Int. Cl.
*A61F 2/16* (2006.01)
*A61F 2/00* (2006.01)
(52) U.S. Cl.
CPC ...... *A61F 2/1613* (2013.01); *A61F 2002/009* (2013.01); *A61F 2002/1699* (2015.04)
(58) Field of Classification Search
CPC .............. A61F 2/1613; A61F 2002/009; A61F 2002/1699
See application file for complete search history.

(56) References Cited

U.S. PATENT DOCUMENTS 4,343,050 A * 8/1982 Kelman .................... A61F 2/16
623/6.45
5,089,023 A * 2/1992 Swanson ............... A61F 2/1618
359/565
(Continued)

FOREIGN PATENT DOCUMENTS

| EP | 2384166 | 11/2011 |
| WO | WO 2008/036671 | 3/2008 |
| WO | WO 2016/132185 | 8/2016 |

OTHER PUBLICATIONS

Examination Report Under Sections 12 & 13 of the Patents Act, 1970 and the Patents Rules, 2003 dated Dec. 4, 2017 From the Government of India, Intellectual Property India, Patents, Designs, Trade Marks, Geographical Indications Re. Application No. 433/DEL/2015. (5 Pages).
(Continued)

*Primary Examiner* — Amy R Weisberg

(57) ABSTRACT

An optical implantable member (102) is provided. The optical implantable member (102) includes an optic (104). The optic (104) includes an anterior surface (108) and a posterior surface (110), an optical centre (112) and a peripheral edge (116). The optical implantable member (102) is configured to be placed within a capsular bag of the eye. The optic (104) of the optical implantable member (102) includes a barrier (202). The barrier (202) is formed by a protrusion (202) on the posterior surface (110) of the optic (104). The protrusion (202) is concentric to an optical axis (114) of the optic (104). An outer wall (204 or 208) of the protrusion (202) is between the peripheral edge (116) and the optical centre (112). The barrier (202) restricts epithelial cells from migrating towards a central region of the capsular bag.

19 Claims, 8 Drawing Sheets

(56) References Cited

U.S. PATENT DOCUMENTS

| | | | | |
|---|---|---|---|---|
| 5,370,687 A * | 12/1994 | Poler | ............... | A61F 2/1613 623/6.16 |
| 5,391,202 A * | 2/1995 | Lipshitz | ............... | A61F 2/1648 623/6.34 |
| 5,422,687 A * | 6/1995 | Tanaka | ............... | G02C 7/042 351/159.48 |
| 5,728,156 A * | 3/1998 | Gupta | ............... | A61F 2/1648 351/159.17 |
| 5,928,282 A * | 7/1999 | Nigam | ............... | A61F 2/16 623/6.43 |
| 6,007,579 A * | 12/1999 | Lipshitz | ............... | A61F 2/1613 623/6.11 |
| 6,030,416 A * | 2/2000 | Huo | ............... | A61L 27/18 424/423 |
| 6,190,410 B1 * | 2/2001 | Lamielle | ............... | A61F 2/1613 623/6.11 |
| 6,357,875 B1 * | 3/2002 | Herrick | ............... | A61F 2/1613 351/159.02 |
| 6,596,026 B1 * | 7/2003 | Gross | ............... | A61F 2/1648 623/6.25 |
| 6,719,792 B2 * | 4/2004 | Baikoff | ............... | A61F 2/1602 623/6.28 |
| 6,881,225 B2 * | 4/2005 | Okada | ............... | A61F 2/1613 623/6.4 |
| 8,685,087 B2 * | 4/2014 | Vaillant | ............... | A61F 2/1613 623/6.12 |
| 2005/0154457 A1 * | 7/2005 | Aharoni | ............... | A61F 9/08 623/6.35 |
| 2005/0177230 A1 * | 8/2005 | Young | ............... | A61F 2/16 623/6.16 |
| 2006/0142855 A1 * | 6/2006 | Vaudant | ............... | A61F 2/1616 623/6.16 |
| 2008/0077238 A1 * | 3/2008 | Deacon | ............... | A61F 2/1613 623/6.16 |
| 2008/0269882 A1 * | 10/2008 | Simpson | ............... | A61F 2/1613 623/6.17 |
| 2008/0281413 A1 * | 11/2008 | Culbertson | ............... | A61F 2/16 623/6.12 |

OTHER PUBLICATIONS

Hearing Notice dated Jan. 30, 2018 dated Dec. 4, 2017 From the Government of India, Intellectual Property India, Patent Office, Intellectual Property Office Building Re. Application No. 433/DEL/2015. (2 Pages).

International Preliminary Report on Patentability dated Aug. 22, 2017 From the International Bureau of WIPO Re. Application No. PCT/IB2015/056159. (6 Pages).

International Search Report and the Written Opinion dated Oct. 13, 2015 From the International Searching Authority Re. Application No. PCT/IB2015/056159. (7 Pages).

* cited by examiner

SECTION A-A

SECTION B-B

OPTICAL IMPLANTABLE MEMBER

BACKGROUND

Field

The disclosed subject matter in general relates to intraocular/ophthalmic implants, and more particularly, but not exclusively, the subject matter relates to intraocular lens/ophthalmic implants (IOL) with optic that delays development of secondary or after cataract, and facilitates better positioning.

Discussion of Related Field

Clouding of the natural lens in the eye, which leads to decrease in vision, is termed as cataract. A cataractous lens is located within a capsular sac or lens capsule in the posterior chamber of the eye. A method of treating a cataract eye is to remove the clouded natural lens and replace it with an artificial intraocular lens (IOL) in a surgical procedure. Following removal of the cataractous lens, the artificial IOL is typically implanted within the lens capsule in order to mimic the refractive function of the natural lens.

Although IOL implant provides significant benefits to most cataract patients, in a considerable percentage of all patients who have IOL implants, secondary cataract or after cataract may develop within months to years after surgery. Secondary cataract is caused by the deposit and proliferation of cells and fibres on the posterior capsular membrane, thereby obstructing light passing through the IOL implant and obscuring the patient's vision. These cell deposits may originate from the proliferation of residual lens epithelial cells on the internal surface of the lens capsule after surgery and/or the accumulation of inflammatory cells and protein deposits on the IOL implant. Of these two sources, the major cause of secondary cataract may be the proliferation and migration of the residual lens epithelial cells, which originate from the anterior surface of the residual capsular bag or from the equator of capsular bag, towards the central part of posterior surface of the capsular bag.

Conventionally, ophthalmic surgeons typically take considerable care in trying to remove all residual lens epithelial cells prior to the implantation of an artificial IOL implant. However, despite these efforts, some amount of lens epithelial cells usually are left on the internal surface of the capsular bag due to the fact that these cells are difficult to identify and are often difficult to reach due to their position on the inside surface of the capsular bag.

Conventionally, various mechanical means and pharmaceutical means are employed to minimize the formation of secondary cataract. Efforts have been directed at creating an IOL having a posterior peripheral wall with a square edge to present a mechanical barrier to the cells. This wall has, at least to some extent, enabled reduction of growth and migration of the lens epithelial cells towards the centre of the optic of the IOL. However, even with this square edge, there have been several instances of formation of secondary cataract and incidence of after cataract not being eliminated.

In light of the above discussion, there is a need for a technique that can be employed in mechanically restricting epithelial cells from migrating towards the centre of the IOL, thereby preventing opacification of the visual axis.

Moreover, conventional IOLs do not conform to the normal structure and function of the eye. In a human eye, the peripheral part of the retina extends more on the nasal side (side of nose) than on the temporal side (side of ear), which causes some people to experience blank space on the side of the ear, commonly referred to as negative dysphotopsia.

Further, in significant number of cases, the centre of pupil is slightly towards the side of the nose (nasal) and not in the geometrical centre of the cornea/eye, and line of sight (visual axis) is still more nasal to the centre of pupil. This is known as positive angle kappa. In some cases, the line of sight passes away from the centre of eye/cornea and towards temporal side, which is known as negative angle kappa.

Conventional IOLs have round optic and its optical centre is at its geometrical centre. Thus after implantation, the optical centre does not come in line of the line of sight or visual axis, which leads to deterioration of quality of vision. Besides this, at present there is no provision to make surgeon aware of the position of optical centre of IOL, thereby making it difficult to align the optical centre of the IOL with visual axis.

In light of the above discussion, there is a need for a technique where the optic of IOL is designed in such fashion that it ameliorates negative dysphotopsia, compensates for angle kappa and at the same time has some provision to guide surgeon to aim for proper centring.

SUMMARY

An embodiment provides an optical implantable member. The optical implantable member includes an optic. The optic includes an anterior surface and a posterior surface, an optical centre and a peripheral edge. The optical implantable member is configured to be placed within a capsular bag of the eye. The optic also includes a barrier. The barrier is formed by a protrusion on the posterior surface of the optic. An outer wall of the protrusion is between the peripheral edge and the optical centre. The barrier restricts epithelial cells from migrating towards a central region of the capsular bag. The protrusion is concentric to an optical axis of the optic and hence helps in proper centring of the optical implantable member.

BRIEF DESCRIPTION OF DRAWINGS

Embodiments are illustrated by way of example and not limitation in the Figures of the accompanying drawings, in which like references indicate similar elements and in which.

DETAILED DESCRIPTION

Figure 1:
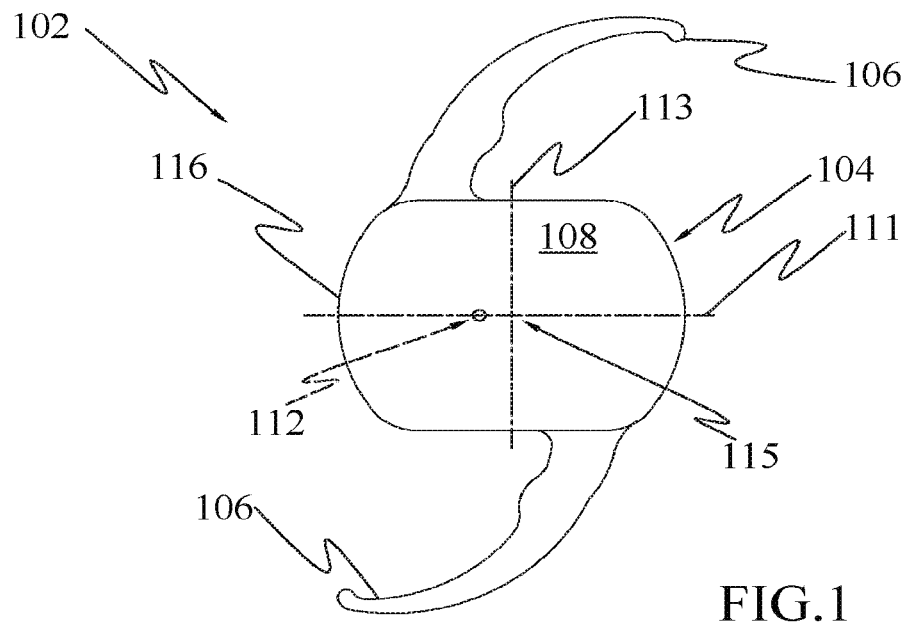
FIG. 1 is an illustration of the anterior surface 108 of exemplary optical implantable member 102, in accordance with an embodiment.

An embodiment provides an optical implantable member for implantation inside the eye. The optical implantable member reduces the possibility of formation of secondary cataract. The optical implantable member may be an intraocular lens that includes an optic and a plurality of support members. The intraocular lens may be configured to be placed over a posterior wall of the capsular bag of the eye. The optic portion of the intraocular lens may be held against the wall of the capsular bag by means of the support members. The intraocular lens may include a barrier. The barrier may be in the form of a protrusion provided around the optical centre of the optic and away from the periphery of the optic. The protrusion may be concentric to the optical axis of the optic. The protrusion forms a barrier around the central region of the capsular bag, thereby restricting epithelial cells from migrating towards a central region of the capsular bag. Such restriction on migration of the epithelial cells mitigates formation of secondary cataract. This barrier is seen as a circle to the surgeon and helps him in better centring/positioning of the optical implantable member.

Another embodiment provides an optic that is oblong. For example, the optic may be elliptical or oval. The optic may be asymmetric with respect to a vertical axis of the capsular bag. Vertical axis of the capsular bag is defined as an imaginary line dividing the capsular bag into two equal halves. The vertical axis of the capsular bag may be offset from a vertical axis of the optic, once the optical implantable member is inserted in the capsular bag. The support members are on either sides of the horizontal axis of the capsular bag, thereby enabling the optic to settle asymmetrically in the capsular bag, more on nasal side to ameliorate negative dysphotopsia. The optical centre of the optic is at an offset to its geometrical centre and is towards the nasal side. Thus, optical centre of the optic aligns with visual axis and decreases aberrations and improves quality of vision.

Further, an indication may be provided on the optic to enable identification of a side of the optic towards which the optical centre is offset. The indication also enables a surgeon to place the optic inside the capsular bag such that, it settles more on nasal side of capsular bag thereby ameliorating negative dysphotopsia.

The following detailed description includes references to the accompanying drawings, which form part of the detailed description. The drawings show illustrations in accordance with example embodiments. These example embodiments are described in enough detail to enable those skilled in the art to practice the present subject matter. However, it will be apparent to one of ordinary skill in the art that the present invention may be practiced without these specific details. In other instances, well-known methods, procedures and components have not been described in detail so as not to unnecessarily obscure aspects of the embodiments. The embodiments can be combined, other embodiments can be utilized or structural and logical changes can be made without departing from the scope of the invention. The following detailed description is, therefore, not to be taken as a limiting sense.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated.

Exemplary Optical Implantable Member

Figure 1A:
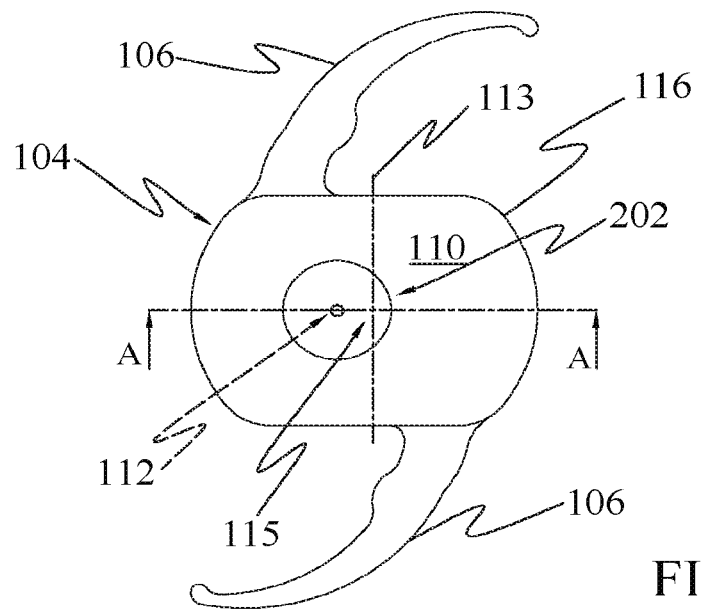
FIG. 1A is an illustration of the posterior surface 110 of the optical implantable member 102 of FIG. 1, wherein a barrier 202 is visible.
Figure 1B:
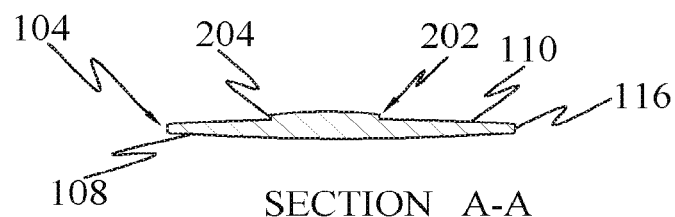
FIG. 1B is a cross sectional view of the optical implantable member 102 of FIG. 1A along axis A-A.
Figure 1C:
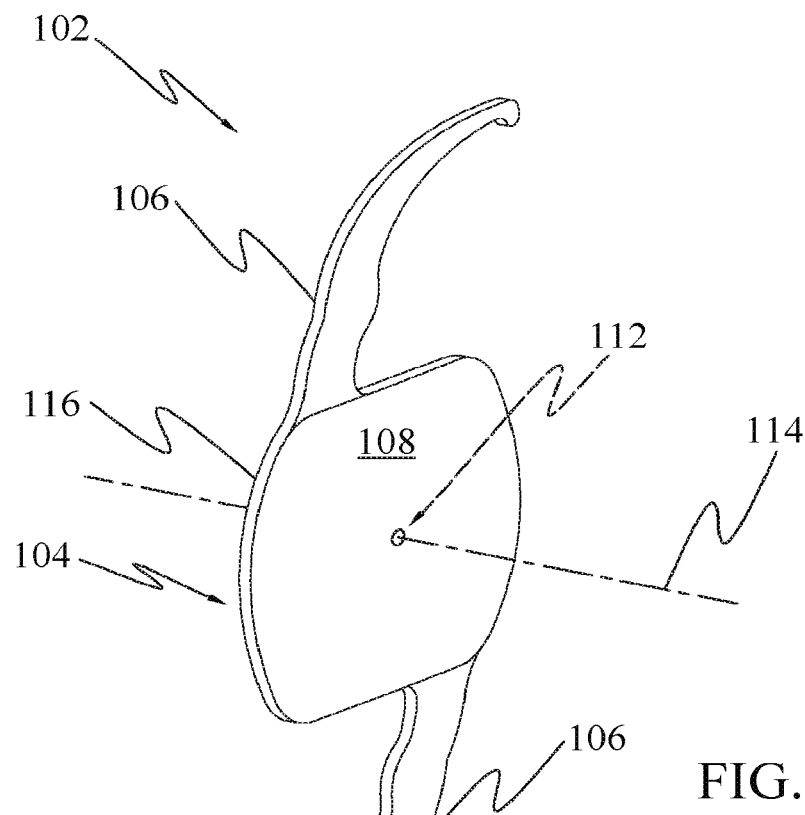
FIG. 1C is an isometric view of the optical implantable member 102 of FIG. 1A.
Figure 1D:
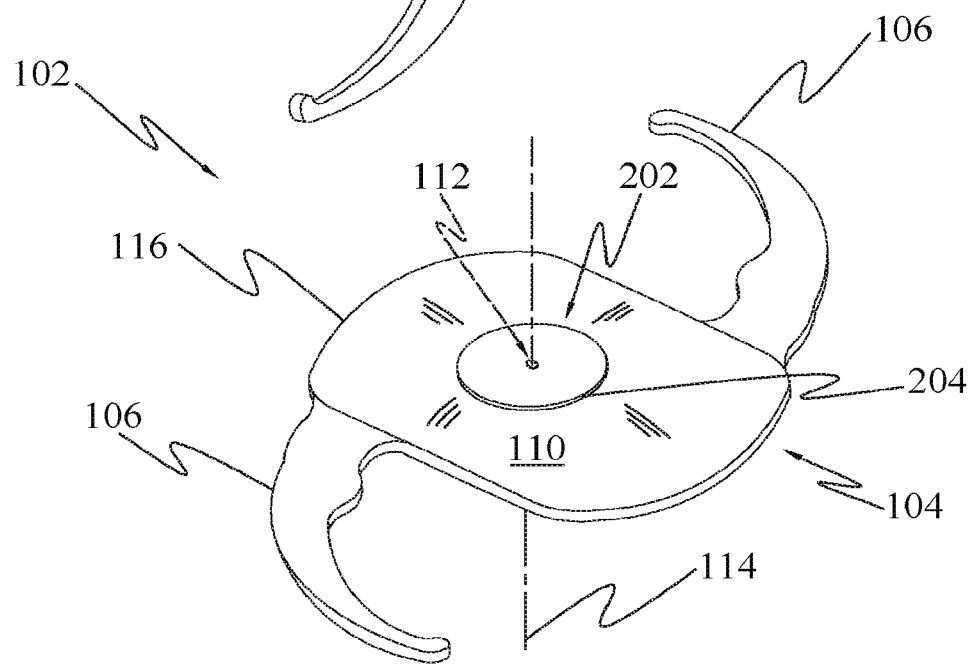
FIG. 1D is an isometric view of the optical implantable member 102 of FIG. 1, in which the barrier 202 is visible.

Now referring to the figures and more specifically to FIGS. 1 to 1D, an embodiment discloses an optical implantable member 102 for implantation inside the eye. The optical implantable member 102 reduces the chances of secondary cataract formation. The optical implantable member 102 may be an intraocular lens. The optical implantable member 102 may include an optic 104 and a plurality of support members 106. The optic 104 may include an anterior surface 108 and a posterior surface 110. The optic 104 has an optical centre 112, an optical axis 114 and a peripheral edge 116. The support member 106 is configured to hold the optic 104 against the posterior walls of the capsular bag in the eye, thereby preventing displacement of the optic 104 once implanted. One or both of the anterior surface 108 and posterior surface 110 may be spherical, aspherical, toric or multifocal. The optic 104 of the optical implantable member 102 may be a portion of the optical implantable member 102 having optical properties.

In an embodiment, the optic 104 of the optical implantable member 102 may be in the shape of an oblong or ellipse. The optic 104 has a horizontal axis ill and a vertical axis 113, passing through a geometric centre 115 of the optic 104. The oblong shaped optic 104 may have a greater length along the horizontal axis 111 as compared to the length along the vertical axis 113. For example, the length of the oblong along the vertical axis 113 may measure 5.8 mm and the length of the oblong along the horizontal axis 111 may measure 6.2 mm. As an example, the shape of the optic 104 may be defined by two parallel edges connected by an arc on each side. The parallel edges may be separated by a distance of 5.8 mm. In other words, the length of the optic 104 along the vertical axis may be 5.8 mm. The largest distance between two arcs may be 6.2 mm.

Figure 3:
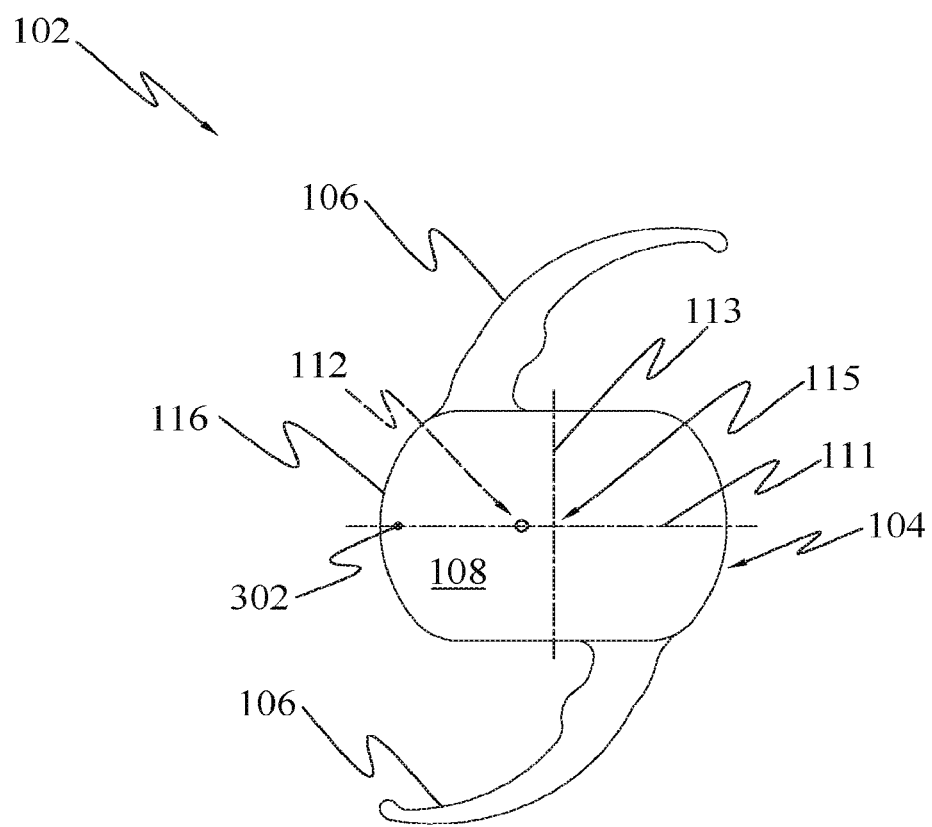
FIG. 3 is an illustration of another exemplary optical implantable member 102 in which optical center 112 of an optic 104 is offset from a geometrical centre 115 of the optic 104, and an indication 302 is provided on the optic 104, in accordance with an embodiment.
Figure 3A:
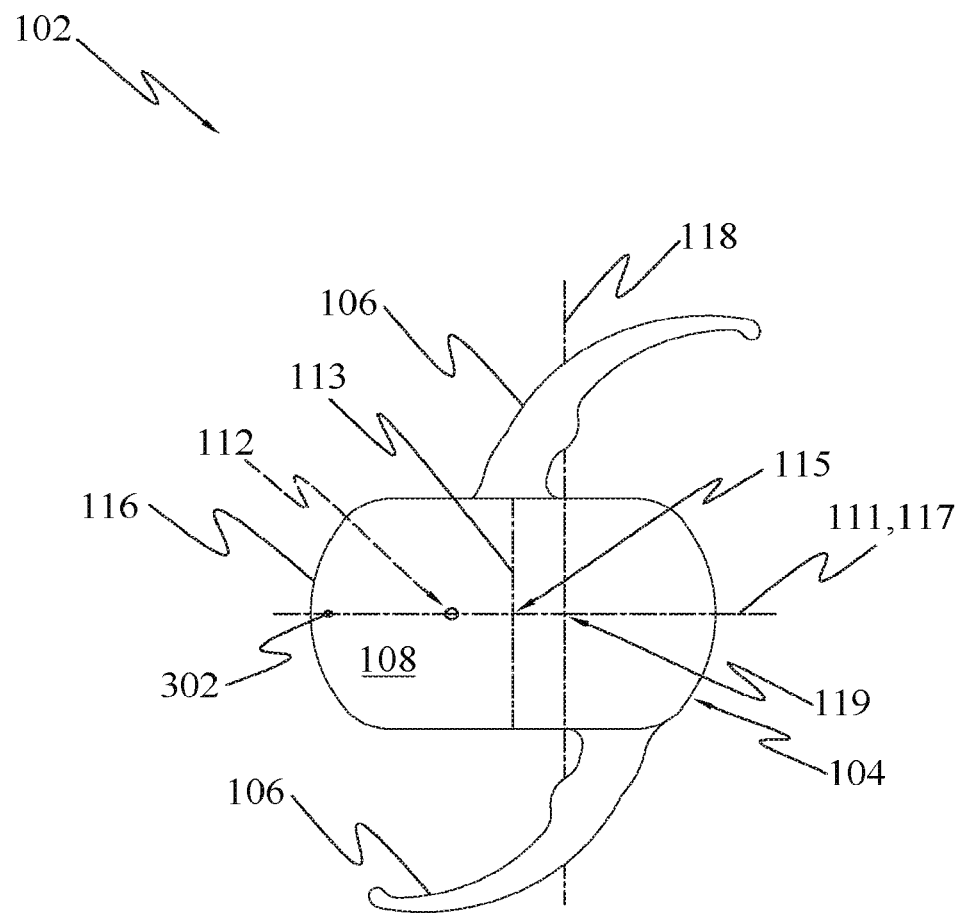
FIG. 3A is an illustration of an exemplary optical implantable member 102, with support members 106 on either side of the optic 104, in which the distance of each of the support members 106, to the geometrical centre 115 of the optic 104 is different, in accordance with an embodiment.
Figure 3B:
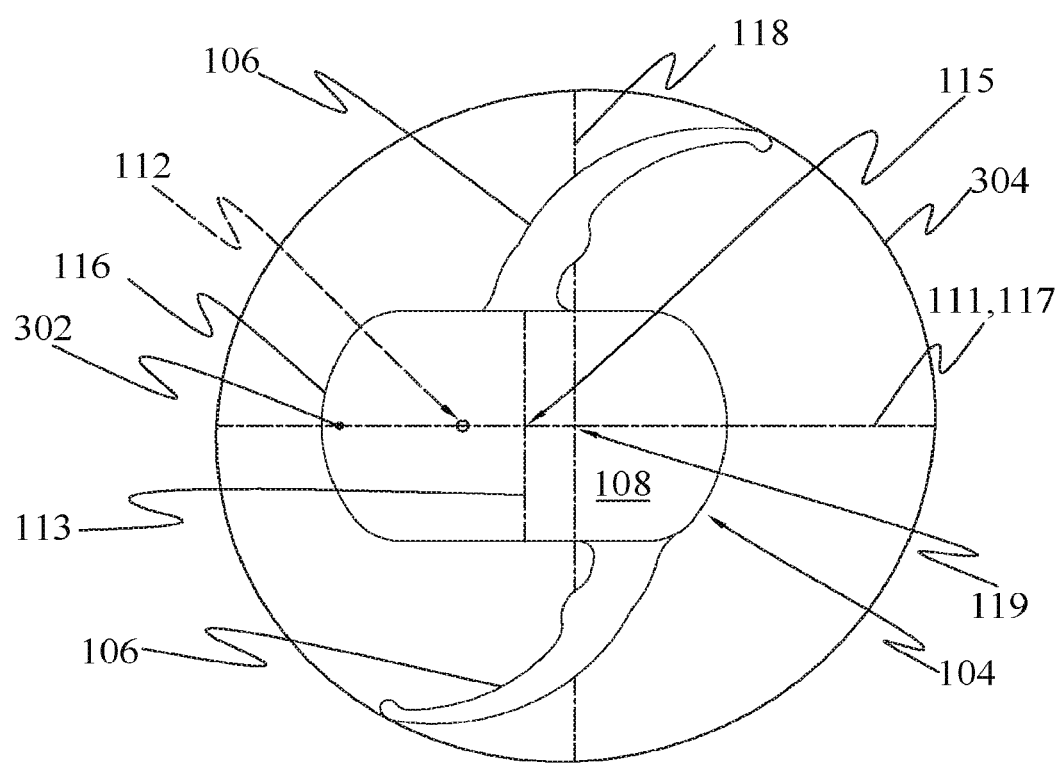
FIG. 3B is a simplified illustration of the optical implantable member 102 of FIG. 3A received in a capsular bag 304, in accordance with an embodiment.

In an embodiment, the capsular bag has a horizontal axis 117 and a vertical axis 118 (shown in FIGS. 3A and 3B). Vertical axis 118 of the capsular bag is defined as an imaginary line dividing the capsular bag into two equal halves. The horizontal axis 117 and the vertical axis 118 of the capsular bag intersect at a geometrical centre 119 of the capsular bag.

In an embodiment, (also referring to FIGS. 3A and 3B), the vertical axis 118 of the capsular bag may be offset from the vertical axis 113 of the optic 104 when the optical implantable member 102 is implanted in the capsular bag. The horizontal axis 117 of the capsular on the other hand, may coincide with the horizontal axis 111 of the optic 104 once the optical implantable member 102 is implanted in the capsular bag. The vertical axis 113 of the optic 104 may be towards the nasal side or towards the temporal side with respect to the vertical axis 118 of the capsular bag once the optical implantable member 102 is implanted.

In an embodiment, the geometrical centre 115 of the optic 104 may be offset from the geometrical centre 119 of the capsular bag of the eye along the horizontal axis 117 (or 111), when the optical implantable member 102 is implanted in the capsular bag. The geometrical centre 115 of the optic 104 may be towards the nasal side or towards the temporal side with respect to the geometrical centre 119 of the capsular bag once the optical implantable member 102 is implanted.

The vertical axis 118 of the capsular bag divides the optic 104 into two asymmetric portions (shown in FIGS. 3A and 3B). For example, one edge of the optic 104, on the horizontal axis 111 may measure 3.2 mm, from the vertical axis 118 of the capsular bag, and another edge on the horizontal axis 111, may measure 3 mm from the vertical axis 118 of the capsular bag, once the optical implantable member 102 is implanted in the capsular bag.

In an embodiment, the longer side on the horizontal axis 111 of the optic 104, as measured from the vertical axis 118 of the capsular bag, may be on the nasal side. This configuration may help in correcting negative dysphotopsia, thereby shifting the optical centre 112 towards nasal side after insertion into the capsular bag.

In an embodiment the optic 104 is designed such that its optical centre 112 is offset from its geometrical centre 115 along the horizontal axis 111 of the optic 104 and is towards the nasal side. The optical centre 112 may be away from the geometric centre 115 in either direction and to any extent. Such a configuration may be useful in achieving better alignment of optical centre 112 of the optic 104 with visual axis, thereby decreasing the aberrations and improving quality of vision. The optical centre 112 of the optic 104 may be offset from the geometrical centre 115 along the horizontal axis 111 to compensate angle kappa to any extent as desirable.

The optic 104 of the optical implantable member 102 is made of suitable transparent material with appropriate refractive index which is bio-compatible to human eye. This material for example can be hydrophilic acrylic, hydrophobic acrylic, silicon, hydrogel or PMMA.

The optic 104 of the optical implantable member 102 may also have some dye incorporated in its material to block particular wavelength of visible spectrum. The optic 104 of the optical implantable member 102 may also be photo chromatic, which means that it becomes pigmented on exposure to light. The optic 106 of the optical implantable member 102 has some focusing power which is usually converging but may also be diverging in some case.

The focusing power may be on the anterior surface 108 of the optic 104 of the optical implantable member 102. The focusing power may also be on the posterior surface 110 of the optic 104 of the optical implantable member 102. Further, the focusing power may be on both surfaces of the optic 104 of the optical implantable member 102.

In an embodiment, the surface of the optic 104 of the optical implantable member 102 may be constructed to provide benefits like asphericity to correct aberrations, or toricity to correct cylindrical power also called astigmatism or multifocality to provide pseudo accommodation and increasing or decreasing the stickiness of the surface, among others.

In an embodiment, the optical implantable member 102 includes a barrier 202 (also shown in FIG. 1A), The barrier 202 may be formed by a protrusion 202. The protrusion 202 may be concentric to the optical axis 114 of the optic 104. The protrusion 202 may extend from the posterior surface 110 of the optical implantable member 102 towards a direction away from the posterior surface 110.

The protrusion 202 may be in the form of a solid cylinder or disc, and may be concentric to the optical axis 114 of the optical implantable member 102. Such a configuration enables tracking of the optical centre 112 during implantation. The protrusion 202 is away or at a distance from the peripheral edge 116 of the optic 104. An outer wall 204 of the protrusion 202 faces the peripheral edge 116 of the optic 104. In other words, the outer wall 204 or confining structure of the protrusion 202 is between the optical centre 112 and the peripheral edge 116.

In an embodiment, the diameter of the protrusion 202 ranges between 2.00 mm and 5.00 mm.

In another embodiment, preferably, the diameter of the protrusion 202 ranges between 3.0 mm and 4.00 mm.

In yet another embodiment, more preferably, the diameter of the protrusion 202 is 3.50 mm.

The protrusion 202 may have a height extending away from the posterior surface 110 of the optic 104, along the optical axis 114 of the optic 104.

In an embodiment, the height of the protrusion 202 may range between 1 micron and 8 microns.

In another embodiment, preferably, the height of the protrusion 202 may range between 2 microns and 6 microns.

In yet another embodiment, more preferably, the height of the protrusion 202 is 2 microns.

In an embodiment, the outer wall 204 of this protrusion 202 is parallel to the optical axis 114 of the optic 104.

In another embodiment, the outer wall 204 of the protrusion 202 is angular to the optical axis 114 of the optic 104.

The protrusion 202 is constructed such that the posterior surface of the protrusion 202 remains in contact with or adheres to the posterior wall of the capsular bag when implanted.

Figure 2:
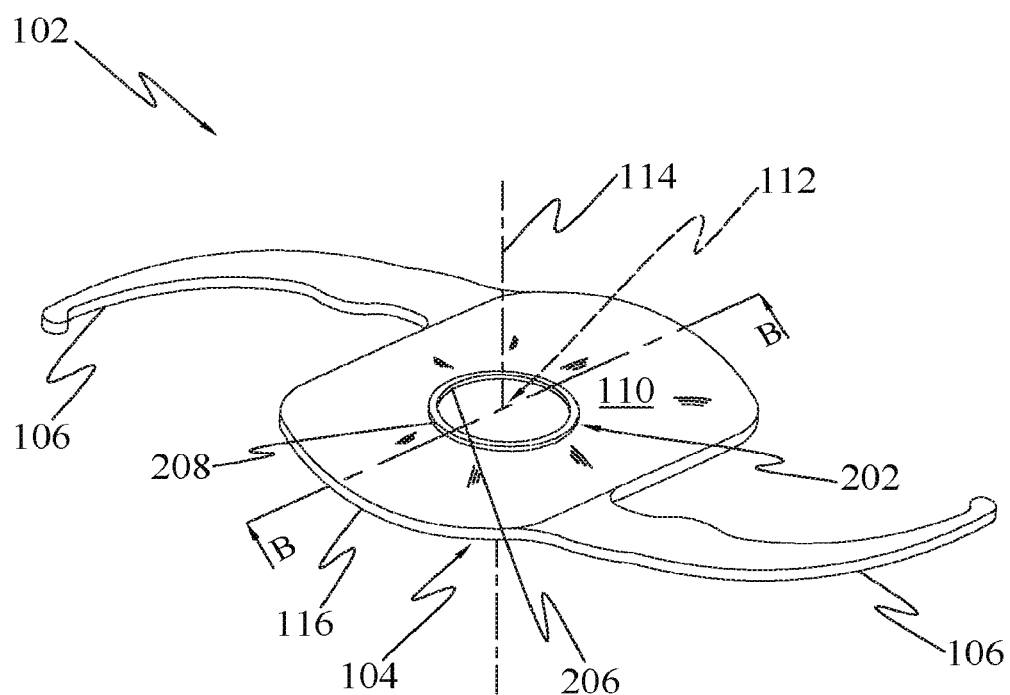
FIG. 2 is an isometric posterior view of another exemplary optical implantable member 102 showing a barrier 202 that resembles the shape of a ring, in accordance with an embodiment.
Figure 2A:
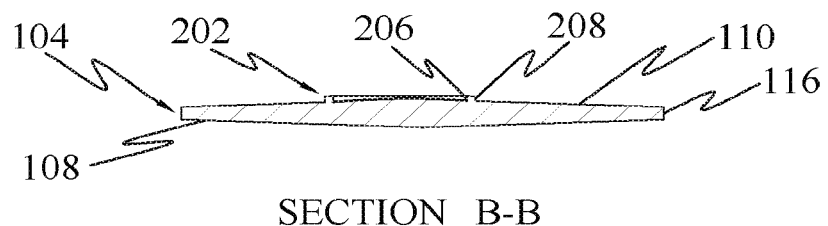
FIG. 2A is a cross sectional view of the optical implantable member 102 of FIG. 2 along axis B-B.

Referring to FIGS. 2 and 2A, the protrusion 202 that forms the barrier 202 may be in the shape of a ring. As an example, the protrusion 202 may resemble the shape of a circular ring. It may be noted that the protrusion 202, as an example, can resemble a shape that may resemble a ring (ex: polygon). The circular ring structure of the protrusion 202 may have an inner diameter (ID) and an outer diameter (OD).

In an embodiment, the ID of the protrusion 202 ranges between 2.00 mm and 5.00 mm.

In another embodiment, preferably, the ID of the protrusion 202 ranges between 3.00 mm and 4.00 mm.

In yet another embodiment, more preferably, the ID of the protrusion 202 is 3.50 mm.

The protrusion 202 may have a height extending away from the posterior surface 110 of the optic 104, along the optical axis 114 of the optic 104.

In an embodiment, the height of the protrusion 202 may range between 1 micron and 8 microns.

In another embodiment, preferably, the height of the protrusion 202 may range between 2 microns and 6 microns.

In yet another embodiment, more preferably, the height of the protrusion 202 is 2 microns.

The protrusion 202 defines an inner wall 206 and an outer wall 208. The inner wall 204 faces the optical centre 112 and the outer wall 208 faces the peripheral edge 116.

In an embodiment the inner wall 206 and the outer wall 208 may be parallel to the optical axis 114.

In an embodiment, at least the outer wall 208 is at an angle with respect to the optical axis 114.

In an embodiment, at least the inner wall 206 is at an angle with respect to the optical axis 114.

In an embodiment, the protrusion 202 that forms the barrier 202 may be in the shape of an ellipse (as opposed to circular) especially in those optical implantable members 102 whose optic 104 has toric power or cylindrical power.

Referring to FIG. 3, a mark or indication 302 is provided near the peripheral edge 116 of the optic 104 to enable identification of a side of the optic 104 towards which the optical centre 112 is offset. The mark or indication 302 may be a permanent mark or an erasable mark.

In an embodiment, the optical centre 112 of the optic 104 may be offset from the geometrical centre 115 towards the nasal side, thereby shifting the optical centre 112 towards the nasal side of capsular bag once inserted. The optical centre 112 of the optic 104 may be offset from the geometrical centre 115 along the horizontal axis 111 to compensate angle kappa to any extent as desirable. Such configurations may be useful in decreasing the aberrations and improving quality of vision by better alignment of optical centre 112 of optic 104 with visual axis.

For those patients whose line of sight is away from the centre of pupil and is towards the nose, the optical implantable member 102 is implanted such that the mark 302 on the optic 104 is on the nasal side (side of the nose).

For those patients whose line of sight is towards the ear from the centre of pupil, the optical implantable member 102 is implanted such that the mark 302 on the optic 104 is on the temporal side (side of the ear).

Referring to FIG. 3A, a pair of support members 106 (also referred to as haptic) may be provided on either edge of the optic 104, on either sides of the horizontal axis 111. In an embodiment, the distance of the support member 106, which is provided on an upper side of the horizontal axis 111, to the geometrical centre 115 of the optic 104, is different from distance of the support member 106, which is provided on a lower side of the horizontal axis 111, to the geometrical centre 115 of the optic 104.

The support members 106 may be disposed asymmetrically with respect to the geometrical centre 115 of the optic 104 and the vertical axis 113 of the optic 104. The placement of the support members 106 may however be symmetric with respect to the vertical axis 118 and the geometrical centre 119 of the capsular bag. In other words, the support members 106 may be equidistant from the geometric centre 119 of capsular bag 304 (FIG. 3B).

Referring to FIG. 3B, the optical implantable member 102 may be received in the capsular bag 304. The vertical axis 118 divides the optic 104 asymmetrically once the optical implantable member 102 is implanted in the capsular bag 304, thereby making the placement of the support members 106 asymmetric to the same extent in relation to the geometric centre 115 and the vertical axis 113 of the optic 104. Such a configuration enables the optic 104 to settle asymmetrically within the capsular bag 304. The optic 104 settles more on nasal side, to ameliorate negative dysphotopsia once the optical implantable member 102 is placed in the capsular bag 304.

Figure 4:
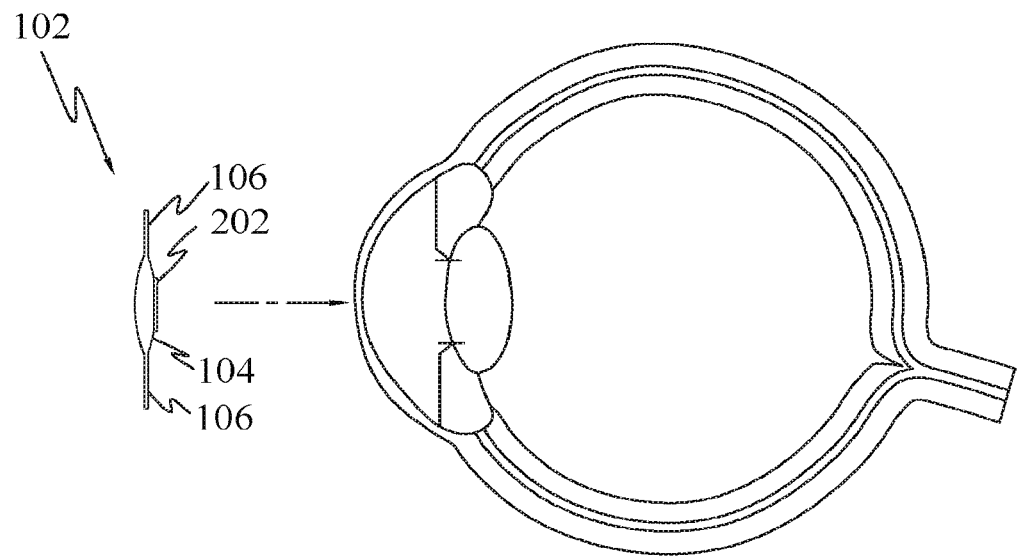
FIG. 4 is an illustration of the exemplary optical implantable member 102 of FIG. 1 to be implanted in the eye, in accordance with an embodiment.
Figure 4A:
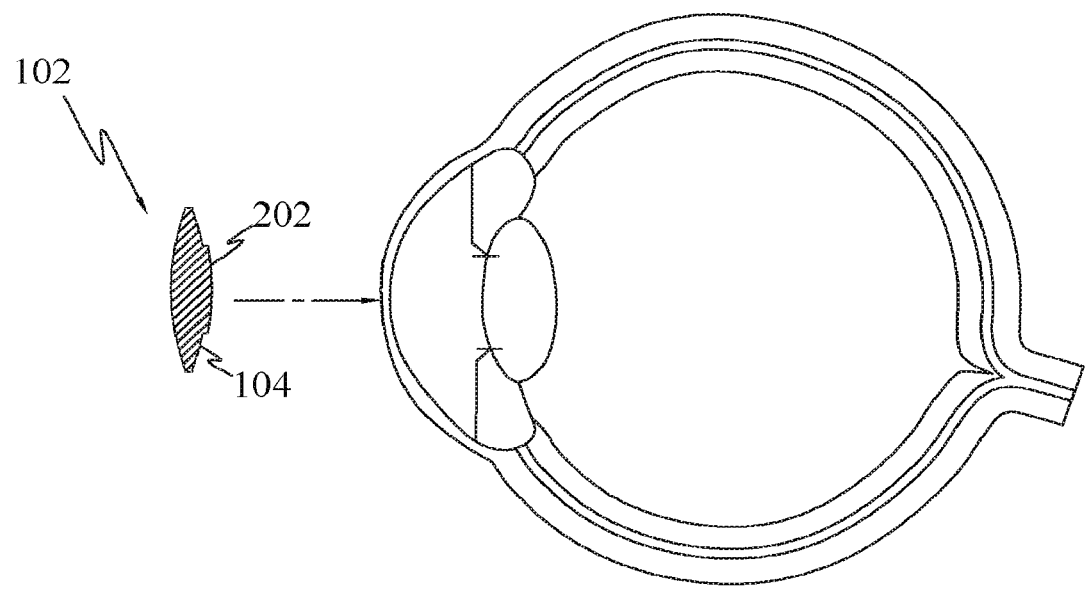
FIG. 4A is an illustration of the exemplary optical implantable member 102 (cross section) of FIG. 1 to be implanted in the eye, in accordance with an embodiment.

Referring to FIGS. 4 and 4A, the optical implantable member 102 is implanted inside the capsular bag of the eye to replace the natural lens. The anterior surface of the capsular bag is opened to remove the natural lens and insert the optical implantable member 102. The optical implantable member 102 may be folded and inserted into the capsular bag through a very small incision made on the cornea. The posterior wall of the capsular bag remains intact to support the optic 104 of the optical implantable member 102. The posterior surface 110 of the optic 104 faces the posterior wall of the capsular bag.

Figure 5:
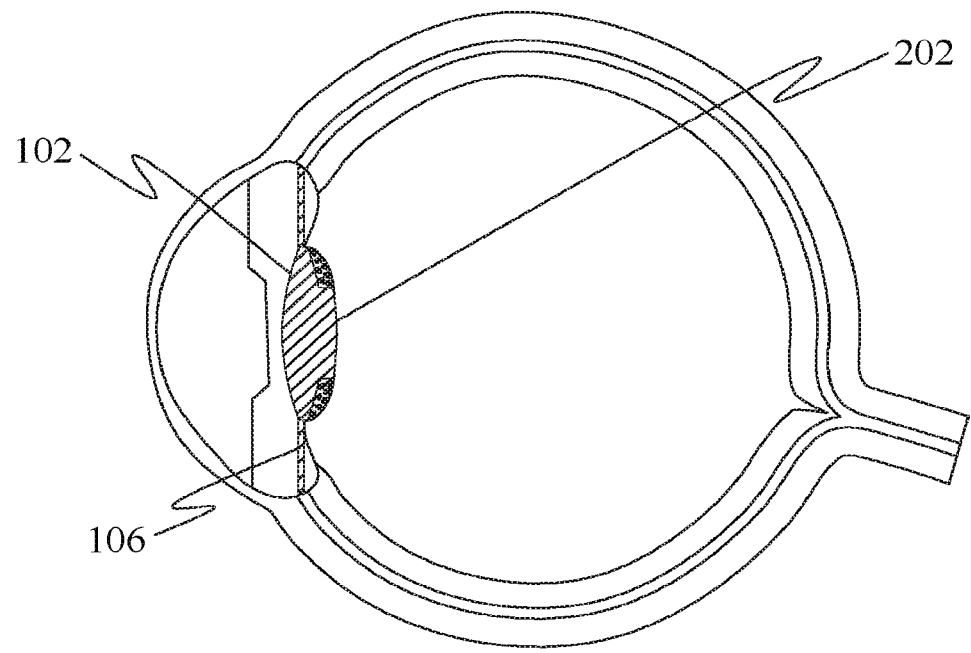
FIG. 5 is an illustration of the exemplary optical implantable member 102 of FIG. 1D restricting the migration of epithelial cells towards the optical centre 112 and the centre of the capsular bag, in accordance with an embodiment.
Figure 5A:
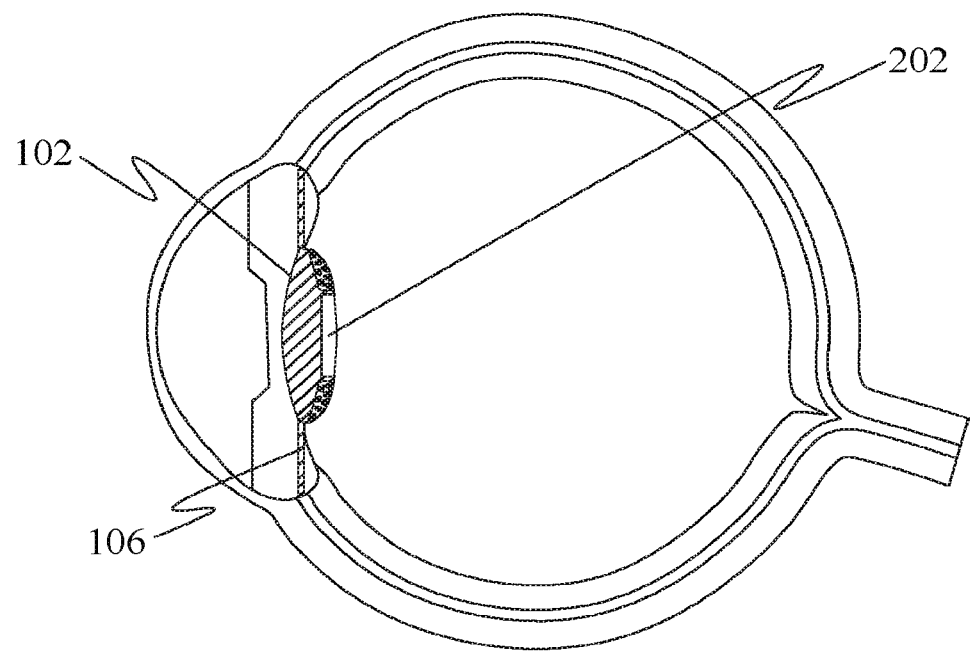
FIG. 5A is an illustration of the exemplary optical implantable member 102 of FIG. 2 restricting the migration of epithelial cells towards the optical centre 112 and the centre of the capsular bag, in accordance with an embodiment.

Referring to FIG. 5, the optical implantable member 102, with the protrusion 202 as illustrated in FIG. 1D, which is in the form of a solid cylinder or disc, covers the central region of the posterior wall of the capsular bag. The protrusion 202 is held against the posterior wall of the capsular bag 304 such that penetration/migration of residual lens epithelial cells and fibres towards the central region of the capsular bag is restricted, thereby reducing or delaying the chances of after-cataract formation. Referring to FIG. 5A, the optical implantable member 102, with the protrusion 202 as illustrated in FIG. 2, which is in the shape of a ring, covers the central region of the posterior wall of the capsular bag.

The optical implantable member 102 may have to be placed such that the optical centre 112 of the optic 104 is in line with the visual axis. The alignment of the implanted optical implantable member 102 may be achieved by techniques well known in the art, such as, rotating the optical implantable member 102 inside the capsular bag. The protrusion 202 which is visible through the anterior surface 108 of the optic 104 as a circle is used as a reference to track the optical centre 112 of the optic 104. As this ring is concentric to the optical axis 114 of the optic 104 co-axially sighted light reflex is brought in the centre of the circle. The surgeon is also guided by permanent indication marks that may be provided on the peripheral edge 116 of the optic 104 of the optical implantable member 102.

In an embodiment, temporary indication marks may be provided on the optical centre 112 or around the optical centre 112 of the optic 104 of the optical implantable member 102. Such a configuration of the optic 104 may enable the surgeon to track the optical centre 112 of the optic 104 even in case of a constricted pupil. In case of toric Intraocular Lens, these temporary marks may help in proper alignment of toric lens with corneal marks in constricted pupil.

Some of the embodiments may also apply to optical implantable members 102 implanted in the ciliary sulcus or anterior chamber of the eye. Some of the embodiments may also apply to optical implantable members 102 clawed to the front or back surface of the iris of the eye or fixated to the sclera by stitches or glue. In some instances artificial lens can also be implanted without removal of natural lens for the purpose of correction of refractive power then it is called phakic Intraocular Lens and some embodiments of this invention may also apply to these.

Embodiments provide an optical implantable member for implantation inside the eye. The optical implantable member significantly reduces the chances of secondary cataract formation.

Embodiments provide an optical implantable member, such as, an intraocular lens including barrier formed by protrusion towards the central region of the lens, wherein the barrier is configured to adhere to the posterior wall of a capsular bag of the eye thereby forming a blockage that restricts migration of residual lens epithelial cells and fibres towards a central region of the capsular bag, which are among the factors responsible for formation of secondary cataract.

Embodiments provide an optical implantable member that has an asymmetric optic designed to ameliorate negative dysphotopsia.

Embodiments provide an optical implantable member, in which the optical centre of the optic is offset from the geometrical centre of the optic and also the geometrical centre of the capsular bag, designed in order to decrease aberrations and achieve proper alignment of the optical centre of the optical implantable member with the visual axis.

It shall be noted that the processes described above is described as sequence of steps, this was done solely for the sake of illustration. Accordingly, it is contemplated that some steps may be added, some steps may be omitted, the order of the steps may be re-arranged, or some steps may be performed simultaneously.

Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

Many alterations and modifications of the present invention will no doubt become apparent to a person of ordinary skill in the art after having read the foregoing description. It is to be understood that the phraseology or terminology employed herein is for the purpose of description and not of limitation. It is to be understood that the description above contains many specifications, these should not be construed as limiting the scope of the invention but as merely providing illustrations of some of the personally preferred embodiments of this invention. Thus the scope of the invention should be determined by the appended claims and their legal equivalents rather than by the examples given.

What is claimed is:

1. An optical implantable member for implant into a capsular bag of an eye, comprising:
   a lens, comprising an anterior surface and a posterior surface, curvature of one or both of said surfaces defining a focusing power of said lens,
   wherein the lens has a peripheral edge, a horizontal axis, a geometric centre which is also an optical centre of said lens, and an optical axis, where said optical axis passes through said optical centre and said geometrical centre, where positions of said optical axis and said optical centre are defined by said curvature,
   wherein said optical implantable member comprises at least two support members attached to said lens;
   wherein a first point of attachment of a first support member to said peripheral edge of said lens is centered about said geometric center, said optical centre, and said optical axis, said first support member extending radially a first length from said first point of attachment;
   wherein a second point of attachment of a second support member to said peripheral edge of said lens is laterally offset from said geometric center, said optical centre, and said optical axis, said second support member extending radially a second length from said second point of attachment;
   wherein said first length and said second length are the same;
   wherein said first point of attachment being centered about said geometrical centre and said second point of attachment being laterally offset from said geometrical centre, thereby offsets the optical centre with respect to a vertical axis of the capsular bag once the optical implantable member is implemented within the capsular bag;
   wherein said first point of attachment is a first distance from said geometrical centre;
   wherein said second point of attachment is a second distance from said geometrical centre; and
   wherein said first distance and said second distance are different.

2. The optical implantable member of claim 1,
   wherein the optical implantable member is configured to be placed within a capsular bag of the eye; and
   wherein said lens comprises a barrier formed by a protrusion from said posterior surface, wherein the protrusion is concentric to said optical axis and said optical centre of the lens, wherein an outer wall of the protrusion is between the peripheral edge and the optical axis and optical centre, and away from the peripheral edge, whereby the barrier restricts epithelial cells from migrating towards a central region of the capsular bag.

3. The optical implantable member according to claim 2, wherein the protrusion is a solid cylinder having a height extended from the posterior surface of the lens.

4. The optical implantable member according to claim 2, wherein diameter of the protrusion ranges between 2.00 mm and 5.00 mm.

5. The optical implantable member according to claim 2, wherein diameter of the protrusion ranges between 3.00 mm and 4.0 mm.

6. The optical implantable member according to claim 2, wherein height of the protrusion ranges between 1 micron and 8 microns.

7. The optical implantable member according to claim 2, wherein height of the protrusion ranges between 2 micron and 6 microns.

8. The optical implantable member according to claim 2, wherein the outer wall is parallel to or at an angle to the optical centre.

9. The optical implantable member according to claim 2, wherein the length of the lens along a horizontal centre is greater than the length along a vertical centre of the lens.

10. The optical implantable member according to claim 2, wherein the lens is asymmetric with respect to a vertical centre of the capsular bag once the optical implantable member is implanted in the capsular bag.

11. The optical implantable member according to claim 2, wherein the optical centre is offset from a geometric centre of the lens.

12. The optical implantable member according to claim 11, further comprising at least two support members attached to said lens,
   wherein a first point of attachment of a first support member to said peripheral edge of said lens is centered about said geometric centre, said optical centre, and said optical axis, said first support member extending radially a first length from said first point of attachment;
   wherein a second point of attachment of a second support member to said peripheral edge of said lens is centered about said geometrical center, said second support member extending radially a second length from said second point of attachment;

wherein said first length and said second length are the same;

wherein said first point of attachment being centered about said geometrical centre and said second point of attachment being laterally offset from said geometrical centre, thereby offsets the optical centre with respect to a vertical axis of the capsular bag once the optical implantable member is implemented within the capsular bag.

13. The optical implantable member according to claim 12, wherein said first point of attachment is a first distance from said geometrical centre;

wherein said second point of attachment is a second distance from said geometrical centre; and wherein said first distance and said second distance are different.

14. The optical implantable member according to claim 2, further comprising an indication on the lens to enable identification of a side of the lens towards which the optical center is offset.

15. The optical implantable member according to claim 2, wherein said lens is made of transparent material.

16. The optical implantable member according to claim 1, wherein the lens is symmetrical.

17. The optical implantable member of claim 1, wherein said first support member and said second support member are a same size and/or shape.

18. The optical implantable member according to claim 1, wherein said first point of attachment is on a first side of said horizontal axis of said lens, wherein said second point of attachment is on a second side of said horizontal axis of said lens.

19. The optical implantable member according to claim 18, wherein a base of said first support member is attached to said lens at said first point of attachment; wherein a base of said second support member is attached to said lens at said second point of attachment.

* * * * *